United States Patent

Yoshikawa et al.

(10) Patent No.: US 6,720,460 B2
(45) Date of Patent: Apr. 13, 2004

(54) HYDROXYPHENYL ADAMANTANES AND PROCESS FOR THE PRODUCTION OF THE SAME

(75) Inventors: Akira Yoshikawa, Wakayama (JP); Kenji Ekawa, Wakayama (JP); Kentaro Watanabe, Wakayama (JP); Kazuhiko Yao, Wakayama (JP); Miwa Hazama, Wakayama (JP)

(73) Assignee: Honshu Chemical Industry Co., Ltd., Tokyo (JP)

(*) Notice: Subject to any disclaimer, the term of this patent is extended or adjusted under 35 U.S.C. 154(b) by 0 days.

(21) Appl. No.: 10/361,484

(22) Filed: Feb. 7, 2003

(65) Prior Publication Data
US 2003/0187307 A1 Oct. 2, 2003

(30) Foreign Application Priority Data

| Feb. 15, 2002 | (JP) | ................................ 2002-038190 |
| Feb. 15, 2002 | (JP) | ................................ 2002-038192 |
| Dec. 26, 2002 | (JP) | ................................ 2002-376246 |
| Jan. 10, 2003 | (JP) | ................................ 2003-604245 |

(51) Int. Cl.⁷ ............................................. C07C 39/12
(52) U.S. Cl. ...................................................... 568/719
(58) Field of Search ......................................... 568/719

(56) References Cited

U.S. PATENT DOCUMENTS

| 3,516,968 A | * | 6/1970 | Moore | ........................ 528/201 |
| 3,516,969 A | * | 6/1970 | Hoagland | ................... 528/201 |
| 3,594,427 A |  | 7/1971 | Moore |  |
| 3,738,960 A | * | 6/1973 | Thompson | .................. 528/174 |
| 3,738,965 A | * | 6/1973 | Thompson | .................. 528/175 |
| 3,753,950 A | * | 8/1973 | Thompson | .................. 528/175 |
| 3,795,658 A | * | 3/1974 | Thompson | .................... 528/97 |

FOREIGN PATENT DOCUMENTS

| JP | 10-130371 | 5/1998 |
| JP | 2000-143566 | 5/2000 |

\* cited by examiner

*Primary Examiner*—Michael L. Shippen
(74) *Attorney, Agent, or Firm*—Knobbe, Martens, Olson & Bear LLP

(57) ABSTRACT

Hydroxyphenyl adamantanes are represented by the general formula (1):

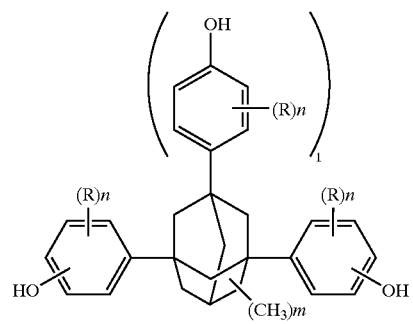

General formula (1)

wherein R is an alkyl group, cycloalkyl group or phenyl group; m is 0 or an integer 1 or 2; l is 0 or 1; when l is 1, hydroxy groups of substituted hydroxyphenyl groups at positions 1 and 3 are together in para-position; n is 0 or an integer 1, 2 or 3; and when l is 0, n is an integer 1, 2 or 3.

5 Claims, No Drawings

HYDROXYPHENYL ADAMANTANES AND PROCESS FOR THE PRODUCTION OF THE SAME

BACKGROUND OF THE INVENTION

1. Field of the Invention

The present invention relates to novel hydroxyphenyl adamantanes which are useful as excellent materials in improving heat resistance and mechanical strength of epoxy resins, photosensitive resins, aromatic polycarbonate resins, or the like.

More specifically, the present invention relates to novel 1,3-bis(hydroxyphenyl)adamantanes and methods for the production thereof.

Further, the present invention also relates to novel 1,3,5-tris(4-hydroxyphenyl)adamantanes and methods for the production thereof.

2. Description of the Related Art

Hydroxyphenyl adamantanes, namely bisphenols and trisphenols having an adamantane ring skeleton, are desired to be highly heat resistant. One of such adamantane bisphenols already known is 1,3-bis(4-hydroxyphenyl)-5,7-dimethyl adamantane which is synthesized using 1,3-dibromo-5,7-dimethyl adamantane and phenol as raw materials as described in U.S. Pat. No. 3,594,427. Further, 1,3-bis(4-hydroxyphenyl)adamantane which is synthesized using 1,3-adamantane-diol and phenol as raw materials is described in Japanese Patent Application Laid-open No. 2000-143566. Furthermore, 2,2-bis(4'-hydroxyphenyl) adamantane which is synthesized using 2-adamantanone and phenol as raw materials is described in Japanese Patent Application Laid-open No. H10-130371.

However, these known adamantane bisphenols are those which have no substituent group in their hydroxyphenyl groups.

In recent years, characteristic requirements for compounds used as materials for resins such as epoxy resins, photosensitive resins, aromatic polycarbonate resins, or the like have been increasingly heightened and diversified and accordingly, also as for adamantane bisphenols, those having various substituent groups such as alkyl group substituents bonded to hydroxyphenyl groups are desired. However, such compounds and industrially advantageous methods for producing such compounds are not known.

On the other hand, as for compounds having three functional groups on an adamantane ring, 1,3,5-tribromo adamantane and a process for the production of adamantane-1,3-5-triol by using this adamantane as a raw material are described in Japanese Patent Application Laid-open No. H02-196477. Further, a higher carboxylic acid triester of adamantane-1,3,5-triol is described in Japanese Patent Application Laid-open No. H02-104553.

However, trisphenols in which three hydroxyphenyl groups are bonded to an adamantane ring and methods for producing such compounds are not known.

SUMMARY OF THE INVENTION

An object of the present invention is to provide novel 1,3-bis(hydroxyphenyl)adamantanes which are useful as raw material compounds for resins having high heat resistance, and methods for the production thereof. Further, an object of the present invention is to provide novel 1,3,5-tris(4-hydroxyphenyl)adamantanes which are useful as raw material compounds for resins having high thermal resistance, and methods for the production thereof.

Novel hydroxyphenyl adamantanes of the present invention are represented by the following general formula (1):

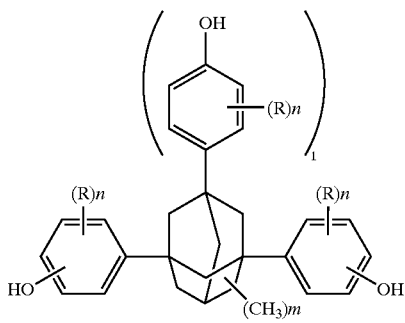

General formula (1)

wherein R is an alkyl group; cycloalkyl group or phenyl group; m is 0 or an integer 1 or 2; l is 0 or 1; when l is 1, hydroxy groups of substituted hydroxyphenyl groups at positions 1 and 3 are together in para-position; n is 0 or an integer 1, 2 or 3; and when l is 0, n is an integer 1, 2 or 3.

Further, 1,3-bis (hydroxyphenyl)adamantanes of the present invention are 1,3-bis(hydroxyphenyl)adamantanes represented by the following general formula (2) in which 4-hydroxyphenyl groups having substituent groups are bonded to positions 1 and 3 of the adamantane ring:

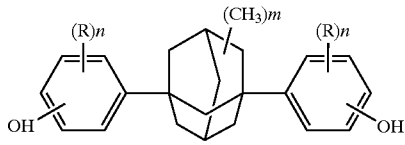

General formula (2)

In the general formula (2) above, R is an alkyl group, cycloalkyl group or phenyl group, n is an integer 1, 2 or 3, and m is 0 or an integer 1 or 2.

Further, these compounds can be efficiently produced by reacting a 1,3-adamantane-diol and substituted phenols in the presence of an acid catalyst under reaction conditions which are industrially feasible without difficulty.

Further, the abovementioned 1,3,5-tris(4-hydroxyphenyl) adamantanes of the present invention are 1,3,5-tris(4-hydroxyphenyl)adamantanes represented by the following general formula (3) in which 4-hydroxyphenyl groups with or without substituent groups are bonded at positions 1, 3 and 5 of the adamantane ring:

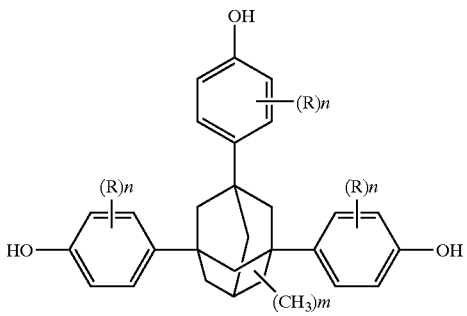

General formula (3)

In the general formula (3) above, R is an alkyl group, cycloalkyl group or phenyl group, n is 0 or an integer 1, 2 or 3, and m is 0 or an integer 1 or 2.

These novel 1,3,5-(4-hydroxyphenyl)adamantanes can be efficiently produced by reacting a 1,3,5-adamantane-triol and phenols in the presence of an acid catalyst under reaction conditions which are industrially feasible without difficulty.

DETAILED DESCRIPTION OF THE PREFERRED EMBODIMENT

Novel hydroxyphenyl adamantanes of the present invention are represented by the following general formula (1):

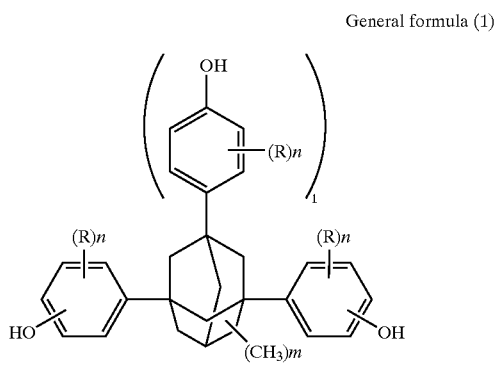

General formula (1)

In the hydroxyphenyl adamantanes represented by the general formula (1) above, R is an alkyl group, cycloalkyl group, or phenyl group, and when R is an alkyl group, the alkyl group is preferably a straight chain or branched chain alkyl group having 1 to 12 carbon atoms, more preferably an alkyl group having 1 to 4 carbon atoms. Examples of such groups include a methyl group, ethyl group, propyl group, and butyl group. The propyl group or butyl group can be a straight chain or branched chain. Further, when R is a cycloalkyl group, a cycloalkyl group having 5 to 6 carbon atoms is preferable, and examples of such groups include a cyclopentyl group and cyclohexyl group. Further, m is 0 or an integer 1 or 2, preferably 0.

l is 0 or 1; when l is 1, hydroxyl groups of substituted hydroxyphenyl groups at positions 1 and 3 are together in para-position; n is 0 or an integer 1, 2 or 3; and when l is 0, n is an integer 1, 2 or 3. Further, when n is 2 or 3, R can be either the same or different, and accordingly hydroxyphenyl adamantanes of the present invention represented by the general formula (1) above can specifically be 1,3-bis (hydroxyphenyl)adamantanes represented by the general formula (2) above and 1,3,5-tris(4-hydroxyphenyl) adamantanes represented by the general formula (3) above.

Examples of the abovementioned 1,3-bis(hydroxyphenyl) adamantanes according to the present invention include 1,3-bis(2-methyl-4-hydroxyphenyl)adamantane, 1,3-bis(3-methyl-4-hydroxyphenyl)adamantane, 1,3-bis(4-methyl-2-hydroxyphenyl)adamantane, 1,3-bis(5-methyl-2-hydroxyphenyl)adamantane, 1,3-bis(3-ethyl-4-hydroxyphenyl)adamantane, 1,3-bis(3-isopropyl-4-hydroxyphenyl)adamantane, 1,3-bis(3-s-butyl-4-hydroxyphenyl)adamantane, 1,3-bis(3-t-butyl-4-hydroxyphenyl)adamantane, 1,3-bis(3,6-dimethyl-4-hydroxyphenyl)adamantane, 1,3-bis(3,5-dimethyl-4-hydroxyphenyl)adamantane, 1,3-bis(3,6-dimethyl-2-hydroxyphenyl)adamantane, 1,3-bis(2,3,5-trimethylhydroxyphenyl)adamantane, 1,3-bis(2,3,6-trimethyl-4-hydroxyphenyl)adamantane, 1,3-bis(3,4,6-trimethyl-2-hydroxyphenyl)adamantane, 1,3-bis(3-cyclohexyl-4-hydroxyphenyl)adamantane, 1,3-bis(2-methyl-5-cyclohexyl-4-hydroxyphenyl)adamantane, 1,3-bis (3-phenyl-4-hydroxyphenyl)adamantane, 1,3-bis(3-methyl-4-hydroxyphenyl)-5,7-dimethyladamantane, 1,3-bis(3-isopropyl-4-hydroxyphenyl)-5,7-dimethyladamantane, 1,3-bis(3,6-dimethyl-4-hydroxyphenyl)-5,7-dimethyladamantane, 1,3-bis(2,3,5-trimethyl-4-hydroxyphenyl)-5,7-dimethyladamantane, 1,3-bis(2,3,6-trimethyl-4-hydroxyphenyl)-5,7-dimethyladamantane, 1,3-bis(3-cyclohexyl-4-hydroxyphenyl)-5,7-dimethyladamantane, 1,3-bis(2-methyl-5-cyclohexyl-4-hydroxyphenyl)-5,7-dimethyladamantane, 1,3-bis(3-phenyl-4-hydroxyphenyl)-5,7-dimethyladamantane, 1,3-bis (3-methyl-4-hydroxyphenyl)-4-methyladamantane, 1,3-bis (3-isopropyl-4-hydroxyphenyl)-4-methyl-adamantane, 1,3-bis(3,6-dimethyl-4-hydroxyphenyl)-4-methyl-adamantane, 1,3-bis(2,3,5-trimethyl-4-hydroxyphenyl)-4-methyl-adamantane, 1,3-bis(2,3,6-trimethyl-4-hydroxyphenyl)-4-methyl-adamantane, 1,3-bis(2-methyl-5-cyclohexyl-4-hydroxyphenyl)-4-methyl-adamantane, and 1,3-bis(3-phenyl-4-hydroxyphenyl)-4-methyl-adamantane.

Furthermore, examples of the abovementioned 1,3,5-tris (4-hydroxyphenyl)adamantanes according to the present invention include 1,3,5-tris(4-hydroxyphenyl)adamantane, 1,3,5-tris(3-methyl-4-hydroxyphenyl)adamantane, 1,3,5-tris (3-isopropyl-4-hydroxyphenyl)adamantane, 1,3,5-tris(3-s-butyl-4-hydroxyphenyl)adamantane, 1,3,5-tris(3,5-dimethyl-4-hydroxyphenyl)adamantane, 1,3,5-tris(3,6-dimethyl-4-hydroxyphenyl)adamantane, 1,3,5-tris(3-methyl-5-t-butyl-4-hydroxyphenyl)adamantane, 1,3,5-tris (2,3,5-trimethyl-4-hydroxyphenyl)adamantane, 1,3,5-tris(2, 3,6-trimethyl-4-hydroxyphenyl)adamantane, 1,3,5-tris(3-cyclohexyl-4-hydroxyphenyl)adamantane, 1,3,5-tris(2-methyl-5-cyclohexyl-4-hydroxyphenyl)adamantane, 1,3,5-tris(3-phenyl-4-hydroxyphenyl)adamantane, 1,3,5-tris(4-hydroxyphenyl)-2-methyladamantane, 1,3,5-tris(3-methyl-4-hydroxyphenyl)-2-methyladamantane, 1,3,5-tris(3,5-dimethyl-4-hydroxyphenyl)-2-methyladamantane, 1,3,5-tris (3-cyclohexyl-4-hydroxyphenyl)-2-methyladamantane, 1,3, 5-tris(3-phenyl-4-hydroxyphenyl)-2-methyladamantane, and 1,3,5-tris(4-hydroxyphenyl)-2,7-dimethyl-adamantane.

As for hydroxyphenyl adamantanes according to the present invention, 1,3-bis(hydroxyphenyl)adamantanes can be obtained by reacting a 1,3-adamantane-diol and substituted phenols in the presence of an acidic catalyst.

Further, 1,3,5-tris(4-hydroxyphenyl)adamantanes according to the present invention can be readily produced by reacting a 1,3,5-adamantane-triol and phenols in the presence of an acid catalyst.

As for 1,3-bis(hydroxyphenyl)adamantanes of the present invention, 1,3-adamantane-diols used as one raw material are represented by the following general formula (4):

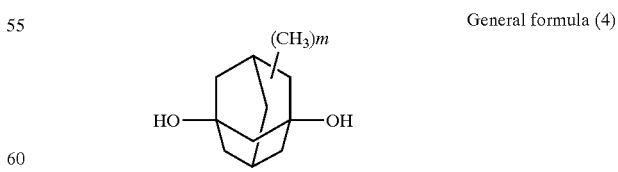

General formula (4)

wherein m is 0 or an integer 1 or 2.

Examples of the abovementioned 1,3-adamantane-diols include 1,3-adamantane-diol, 5,7-dimethyl-1,3-adamantane-diol, 2-methyl-1,3-adamantane-diol, and 4-methyl-1,3-adamantane-diol. 1,3-adamantane-diol is preferable.

On the other hand, substituted phenols used as the other raw material in the present invention are represented by the following general formula (5):

General formula (5)

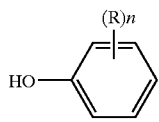

wherein R and n are as defined in the general formula (2) above.

Examples of the compounds of the general formula (5) above include 2-methylphenol, 2-ethylphenol, 2-isopropylphenol, 2-s-butylphenol, 2-t-butylphenol, 3-methylphenol, 2,5-dimethylphenol, 2,6-dimethylphenol, 2,6-diisopropylphenol, 2,6-di-t-butylphenol, 2-methyl-6-t-butylphenol, 3,5-dimethylphenol, 3-methyl-6-t-butylphenol, 2,3,5-trimethylphenol, 2,3,6-trimethylphenol, 2-cyclohexylphenol, 3-methyl-6-cyclohexylphenol, 2-phenylphenol, and 2-isopropyl-6-phenylphenol.

Further, as for 1,3,5-tris(4-hydroxyphenyl)adamantanes of the present invention, 1,3,5-adamantane-triols used as one raw material are represented by the following general formula (6):

General formula (6)

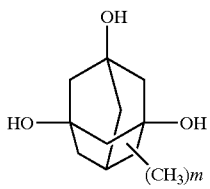

wherein, m is 0 or an integer 1 or 2.

Examples of the 1,3,5-adamantane-triols include 1,3,5-adamantane-triol, 2-methyl-1,3,5-adamantane-triol, 7-methyl-1,3,5-adamantane-triol, and 2,7-dimethyl-1,3,5-adamantane-triol. Of these triols, 1,3,5-adamantane-triol is preferable.

Phenols used as the other raw material in the present invention are represented by the following general formula (7):

General formula (7)

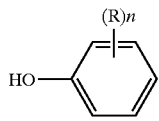

wherein R and n are as defined in the general formula (3).

Examples of the abovementioned phenols include phenol, 2-methylphenol, 2-ethylphenol, 2-isopropylphenol, 2-s-butylphenol, 2-t-butylphenol, 3-methylphenol, 2,5-dimethylphenol, 2,6-dimethylphenol, 2,6-diisopropylphenol, 2,6-di-t-butylphenol, 2-methyl-6-t-butylphenol, 3,5-dimethylphenol, 3-methyl-6-t-butylphenol, 2,3,5-trimethylphenol, 2,3,6-trimethylphenol, 2-cyclohexylphenol, 3-methyl-6-cyclohexylphenol, 2-phenylphenol, and 2-isopropyl-6-phenylphenol.

In the reaction of the abovementioned 1,3-adamantane-diol or 1,3,5-adamantane-triol and phenols, the ratio of the 1,3-adamantane-diol or 1,3,5-adamantane-triol to the phenols is in the range of 3–30, preferably 6–10 by mol.

In the method for the production according to the present invention, an acid catalyst is used in the reaction. Examples of such an acid catalyst include inorganic acids such as hydrogen chloride, hydrochloric acid, sulfuric acid, nitric acid, and phosphoric acid; sulfonic acids such as methanesulfonic acid, trifluoromethanesulfonic acid, benzenesulfonic acid, and p-toluene sulfonic acid; carboxylic acids such as acetic acid and propionic acid; heteropolyacids; and cation exchange resins. Of these acids, strong acids including inorganic acids such as hydrochloric acid and sulfuric acid, sulfonic acids such as p-toluenesulfonic acid, heteropolyacids, highly acidic cation exchange resins are preferable, and in particular, p-toluenesulfonic acid is preferable in terms of reaction velocity and reaction selectivity.

p-Toluenesulfonic acid used is generally a monohydrate. The amount of p-toluenesulfonic acid generally ranges from 30 to 80% by mol, preferably 40 to 60% by mol, of a raw material, i.e., a 1,3-adamantane-diol or 1,3,5-adamantane-triol. In the reaction of a 1,3-adamantane-diol or 1,3,5-adamantane-triol with phenols in the presence of an acid catalyst, the reaction can be carried out either with or without a reaction solvent. Examples of preferable reaction solvents are aromatic hydrocarbons such as toluene. The amount to be used generally ranges from 5 to 50% by weight of a raw material, i.e., phenols. Further, the reaction temperature generally ranges from 60 to 200° C., preferably 70 to 150° C., more preferably 80 to 110° C. Under these reaction conditions, the reaction generally completes within about 1 to 100 hours with 1,3-adamantane-diols. Further, the reaction generally completes within about 10 to 200 hours with 1,3,5-adamantane-triols.

After the reaction, an aromatic hydrocarbon solvent such as toluene and xylene is added to the reaction mixture thus obtained if necessary, and the reaction mixture is dissolved, after which the solution is neutralized by adding an aqueous solution of alkali such as sodium hydroxide or potassium hydroxide with stirring. Next, the water layer is separated and removed from the neutralized oil-water mixture to obtain the oil layer which contains the target product. The targeted 1,3-bis(hydroxyphenyl)adamantane or 1,3,5-tris(4-hydroxyphenyl)adamantane is crystallized from the oil layer thus obtained, filtered, and isolated to obtain crude crystals of the target product.

Further, if necessary, a pure product of the target product can be obtained by the purification procedure such as recrystallization.

EXAMPLE 1

1,3-Bis(3,5-dimethyl-4-hydroxyphenyl)adamantane

In a 3000 ml four-necked flask equipped with a stirrer, a thermometer, and a reflux condenser were placed 176 g (1.05 mol) of 1,3-adamantane-diol and 1023 g (8.39 mol) of 2,6-dimethylphenol, and the air in the reaction container was replaced with nitrogen, after which the temperature was raised to 90° C. Next, while maintaining the temperature, 88 g of p-toluenesulfonic acid monohydrate was added thereto and the reaction was carried out for 7 hours.

After the reaction, the temperature of the reaction mixture thus obtained was lowered to 70° C., and 1023 g of toluene and 2 g of a 75% phosphoric acid aqueous solution were added thereto. Next, a 12% sodium hydroxide aqueous solution was added thereto for neutralization, after which the water layer was separated and the remaining oil layer was washed twice with ion exchange treated water. After washing, the oil layer was cooled down for crystallization, and filtered to obtain crude crystals. The crude crystals were washed with toluene and dried to obtain 230 g of the target product, 1,3-bis(3,5-dimethyl-4-hydroxyphenyl) adamantane, as white crystals (purity: 99.8%).

The yield against 1,3-adamantane-diol was 58% by mol.

Melting point: 189° C. (light transmittance method)

Molecular weight: 375 M⁻ (mass spectrometry)

Proton nuclear magnetic resonance spectrum (solvent: DMSO, 400 MHz); formula 1:

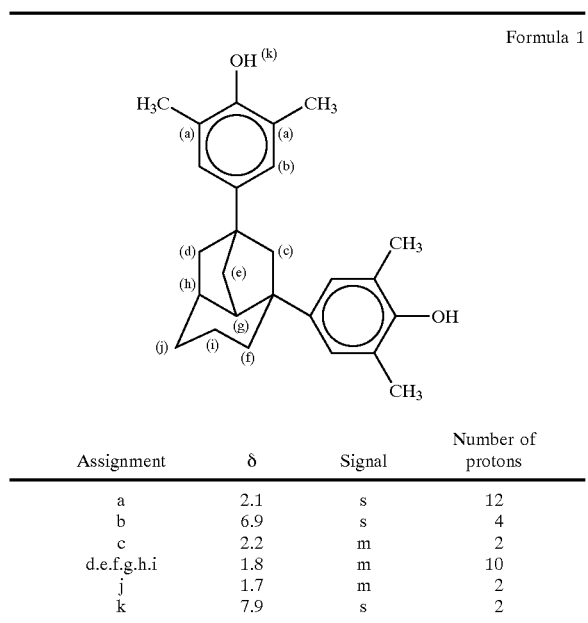

Formula 1

| Assignment | δ | Signal | Number of protons |
|---|---|---|---|
| a | 2.1 | s | 12 |
| b | 6.9 | s | 4 |
| c | 2.2 | m | 2 |
| d,e,f,g,h,i | 1.8 | m | 10 |
| j | 1.7 | m | 2 |
| k | 7.9 | s | 2 |

EXAMPLE 2

1,3-Bis(3-methyl-4-hydroxyphenyl)adamantane

In a 2000 ml four-necked flask equipped with a stirrer, a thermometer, and a reflux condenser were placed 155 g (0.92 mol) of 1,3-adamantane-diol and 798 g (7.4 mol) of 2-methylphenol, and the air in the reaction container was replaced with nitrogen, after which the temperature was raised to 90° C. Next, while maintaining the temperature, 78 g of p-toluenesulfonic acid monohydrate was added thereto and the reaction was carried out for 47 hours.

After the reaction, the temperature of the reaction mixture thus obtained was lowered to 80° C., and 798 g of toluene and 2 g of a 75% phosphoric acid aqueous solution were added thereto. Next, the mixture was neutralized by adding a 12% sodium hydroxide aqueous solution, after which the water layer was separated and the remaining oil layer was washed twice with ion exchange treated water. After washing, the oil layer was cooled down for crystallization, and filtered to obtain crude crystals. The crude crystals were recrystallized with toluene, then washed with toluene and dried to obtain 193 g of the target product, 1,3-bis(3-methyl-4-hydroxyphenyl)adamantane, as white crystals (purity: 99.8%).

The yield against 1,3-adamantane-diol was 60% by mol.

Melting point: 169° C. (light transmittance method)

Molecular weight: 347 M⁻ (mass spectrometry)

Proton nuclear magnetic resonance spectrum (solvent: DMSO, 400 MHz); formula 2

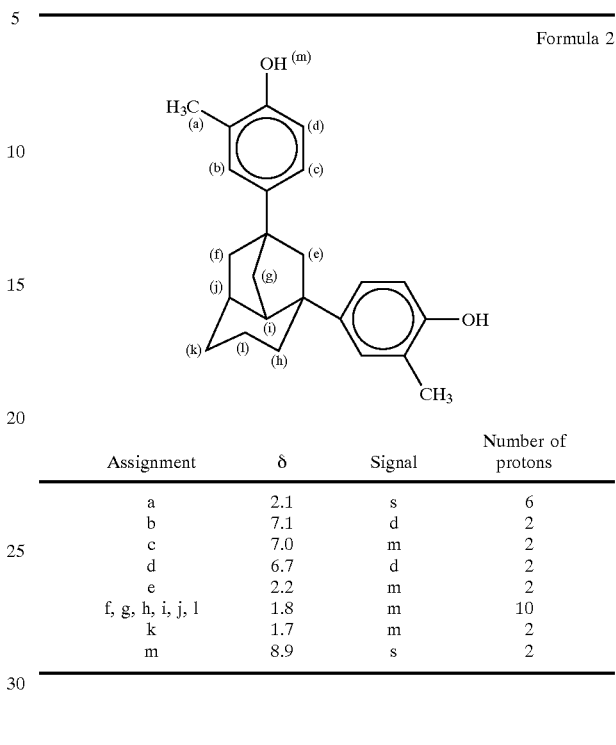

Formula 2

| Assignment | δ | Signal | Number of protons |
|---|---|---|---|
| a | 2.1 | s | 6 |
| b | 7.1 | d | 2 |
| c | 7.0 | m | 2 |
| d | 6.7 | d | 2 |
| e | 2.2 | m | 2 |
| f, g, h, i, j, l | 1.8 | m | 10 |
| k | 1.7 | m | 2 |
| m | 8.9 | s | 2 |

EXAMPLE 3

1,3-Bis(3-phenyl-4-hydroxyphenyl)adamantane

In a 300 ml four-necked flask equipped with a stirrer, a thermometer, and a reflux condenser were placed 25.5 g (0.15 mol) of o-phenylphenol and 2.1 g of p-toluenesulfonic acid monohydrate, and the air in the reaction container was replaced with nitrogen, after which the temperature was raised to 90° C. Next, while maintaining the temperature, a mixed solution of 8.5 g (0.05 mol) of o-phenylphenol and 4.2 g (0.025 mol) of 1,3-adamantane-diol was added thereto over a period of 1 hour and the reaction was carried out for 85 hours.

After the reaction, the temperature of the reaction mixture thus obtained was lowered to 80° C., and 20 g of toluene, 5 g of ion exchange treated water, and 0.2 g of a 75% phosphoric acid aqueous solution were added thereto. Next, the admixture was neutralized by adding a 16% sodium hydroxide aqueous solution, cooled down, and then filtrated to obtain crude crystals. The crude crystals were washed with a mixed solvent of methanol and methylisobutyl ketone, filtered and then dried to obtain 2.0 g of the target product, 1,3-bis(3-phenyl-4-hydroxyphenyl)adamantane, as white crystals (purity: 98.2%).

The yield against 1,3-adamantane-diol was 17% by mol.

Melting point: 201° C. (differential thermal analysis)

Molecular weight: 471 M⁻ (mass spectrometry)

Proton nuclear magnetic resonance spectrum (solvent: DMSO, 400 MHz); formula 3:

Proton nuclear magnetic resonance spectrum (solvent: DMSO, 400 MHz); formula 4:

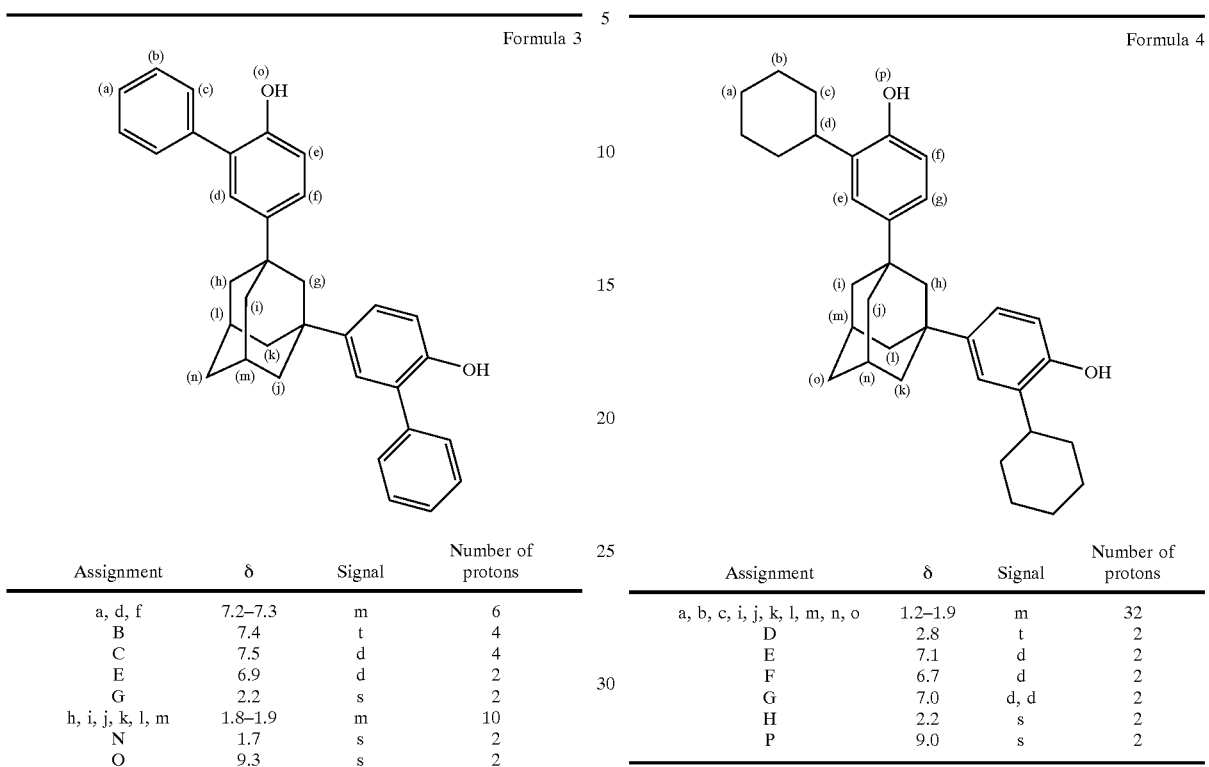

Formula 3

Formula 4

| Assignment | δ | Signal | Number of protons |
|---|---|---|---|
| a, d, f | 7.2–7.3 | m | 6 |
| B | 7.4 | t | 4 |
| C | 7.5 | d | 4 |
| E | 6.9 | d | 2 |
| G | 2.2 | s | 2 |
| h, i, j, k, l, m | 1.8–1.9 | m | 10 |
| N | 1.7 | s | 2 |
| O | 9.3 | s | 2 |

| Assignment | δ | Signal | Number of protons |
|---|---|---|---|
| a, b, c, i, j, k, l, m, n, o | 1.2–1.9 | m | 32 |
| D | 2.8 | t | 2 |
| E | 7.1 | d | 2 |
| F | 6.7 | d | 2 |
| G | 7.0 | d, d | 2 |
| H | 2.2 | s | 2 |
| P | 9.0 | s | 2 |

EXAMPLE 4

1,3-Bis(3-cyclohexyl-4-hydroxyphenyl)adamantane

In a 300 ml four-necked flask equipped with a stirrer, a thermometer, and a reflux condenser were placed 26.4 g (0.15 mol) of o-cyclohexylphenol and 2.1 g of p-toluenesulfonic acid monohydrate, and the air in the reaction container was replaced with nitrogen, after which the temperature was raised to 90° C. Next, while maintaining the temperature, a mixed solution of 8.8 g (0.05 mol) of o-cyclohexylphenol and 4.2 g (0.025 mol) of 1,3-adamantane-diol was added thereto over a period of 1 hour and the reaction was carried out for 25 hours.

After the reaction, the temperature of the reaction mixture thus obtained was lowered to 80° C., and 10 g of toluene, 5 g of ion exchange treated water, and 0.2 g of a 75% phosphoric acid aqueous solution were added thereto. Next, the mixture was neutralized by adding a 16% sodium hydroxide aqueous solution, after which the water layer was separated and the remaining oil layer was washed twice with ion exchange treated water. After washing, the oil layer was cooled down for crystallization, and filtered to obtain crude crystals. The crude crystals were recrystallized with toluene and diisobutylene and then crystals were filtered. Further, the resulting crystals were recrystallized with methanol water, then filtered and dried to obtain 4.1 g of the target product, 1,3-bis(3-cyclohexyl-4-hydroxyphenyl) adamantane, as white crystals (purity: 100%).

The yield against 1,3-adamantane-diol was 34% by mol.

Melting point: 149° C. (differential thermal analysis)

Molecular weight: 482 M⁻ (mass spectrometry)

EXAMPLE 5

1,3-Bis(3-cyclohexyl-6-methyl-4-hydroxyphenyl) adamantane

In a 300 ml four-necked flask equipped with a stirrer, a thermometer, and a reflux condenser were placed 28.5 g (0.15 mol) of 2-cyclohexyl-5-methylphenol and 2.1 g of p-toluenesulfonic acid monohydrate, and the air in the reaction container was replaced with nitrogen, after which the temperature was raised to 70° C. Next, while maintaining the temperature, a mixed solution of 9.5 g (0.05 mol) of 2-cyclohexyl-5-methylphenol and 4.2 g (0.025 mol) of 1,3-adamantane-diol was added thereto over a period of 1 hour, the temperature was raised to 80° C., and then the reaction was carried out for 1 hour.

After the reaction, 60 g of toluene, 5 g of ion exchange treated water, and 0.2 g of a 75% phosphoric acid aqueous solution were added to the reaction mixture thus obtained. Next, the admixture was neutralized by adding a 16% sodium hydroxide aqueous solution, cooled down, and then filtrated to obtain crude crystals. The crude crystals were washed with methanol water, filtered and then dried to obtain 6.2 g of the target product, 1,3-bis(3-cyclohexyl-6-methyl-4-hydroxyphenyl)adamantane, as white crystals (purity: 99.7%).

The yield against 1,3-adamantane-diol was 48.2% by mol.

Melting point: 238° C. (differential thermal analysis)

Molecular weight: 512 M⁻ (mass spectrometry)

Proton nuclear magnetic resonance spectrum (solvent: DMSO, 400 MHz); formula 5:

Formula 5

| Assignment | δ | Signal | Number of protons |
|---|---|---|---|
| a, b, h, i, j, k, l, m, n, o | 1.3–2.2 | m | 22 |
| C | 2.0 | s | 8 |
| D | 2.8 | s | 2 |
| E | 7.0 | s | 2 |
| F | 6.5 | s | 2 |
| G | 2.4 | s | 2 |
| P | 8.8 | s | 2 |

EXAMPLE 6

1,3-Bis(4-methyl-2-hydroxyphenyl)adamantane

In a 300 ml four-necked flask equipped with a stirrer, a thermometer, and a reflux condenser were placed 16.2 g (0.15 mol) of 3-methylphenol and 2.1 g of p-toluenesulfonic acid monohydrate, and the air in the reaction container was replaced with nitrogen, after which the temperature was raised to 85° C. Next, while maintaining the temperature, a mixed solution of 5.4 g (0.05 mol) of 3-methylphenol and 4.2 g (0.025 mol) of 1,3-adamantane-diol was added thereto over a period of 1 hour, the temperature was raised to 90° C., and then the reaction was carried out for 3 hours.

After the reaction, the temperature of the reaction mixture thus obtained was lowered to 80° C., and 30 g of toluene, 5 g of ion exchange treated water, and 0.2 g of a 75% phosphoric acid aqueous solution were added thereto. Next, the admixture was neutralized by adding a 16% sodium hydroxide aqueous solution, after which the water layer was separated and the remaining oil layer was washed with ion exchange treated water. After washing, the oil layer was cooled down for crystallization, and filtered to obtain crystals. The crystals were dried to obtain 5.7 g of the target product, 1,3-bis(4-methyl-2-hydroxyphenyl)adamantane, as white crystals (purity: 99.2%).

The yield against 1,3-adamantane-diol was 64.9% by mol.

Melting point: 183° C. (differential thermal analysis)

Molecular weight: 347 M⁻ (mass spectrometry)

Proton nuclear magnetic resonance spectrum (solvent: DMSO, 400 MHz); formula 6:

Formula 6

| Assignment | δ | Signal | Number of protons |
|---|---|---|---|
| a, c | 6.5 | t | 4 |
| d | 6.9 | d | 2 |
| b, f, g, h, i, j, k | 2.0–2.1 | m | 16 |
| e | 2.3 | s | 2 |
| l | 1.7 | s | 2 |
| m | 9.0 | s | 2 |

EXAMPLE 7

1,3,5-Tris(3,5-dimethyl-4-hydroxyphenyl)adamantane

In a 100 ml four-necked flask equipped with a stirrer, a thermometer, and a reflux condenser were placed 5.0 g (0.027 mol) of 1,3,5-adamantane-triol and 33.2 g (0.27 mol) of 2,6-dimethylphenol, and the air in the reaction container was replaced with nitrogen, after which the temperature was raised to 90° C. Next, while maintaining the temperature, 2.5 g of p-toluenesulfonic acid monohydrate was added thereto and the reaction was carried out for 25 hours.

After the reaction, the temperature of the reaction mixture thus obtained was lowered to 70° C., and 33 g of toluene and 5.0 g of ion exchange treated water were added thereto. Next, a 12% sodium hydroxide aqueous solution was added for neutralization, after which the water layer was separated and the remaining oil layer was washed, twice with ion exchange treated water. After washing, the oil layer was cooled down for crystallization, and filtered to obtain crude crystals. The crude crystals were purified by recrystallization with a mixed solvent of toluene and methylisobutyl ketone, and dried to obtain 5.9 g of the target product, 1,3,5-tris(4-hydroxy-3,5-dimethylphenyl)adamantane, as white crystals (purity: 99.8%).

The yield against 1,3,5-adamantane-triol was 44.0% by mol.

Melting point: 201° C. (light transmittance method)

Molecular weight: 495.2 (M–H)⁻ (mass spectrometry)

Proton nuclear magnetic resonance spectrum (solvent: DMSO, 400 MHz); formula 7:

Formula 7

| Assignment | δ | Signal | Number of protons |
|---|---|---|---|
| a | 7.9 | s | 3 |
| c | 6.9 | s | 6 |
| d | 2.3 | m | 1 |
| b | 2.1 | s | 18 |
| e, f, g, h, i, j | 1.8–1.9 | m | 12 |

EXAMPLE 8

1,3,5-Tris(4-hydroxyphenyl)adamantane

In a 100 ml four-necked flask equipped with a stirrer, a thermometer, and a reflux condenser were placed 5.0 g (0.027 mol) of 1,3,5-adamantane-triol and 25.5 g (0.27 mol) of phenol, and the air in the reaction container was replaced with nitrogen, after which the temperature was raised to 80° C. Next, while maintaining the temperature, 2.5 g of p-toluenesulfonic acid monohydrate was added thereto and the reaction was carried out for 130 hours.

After the reaction, the temperature of the reaction mixture thus obtained was lowered to 70° C., and 33 g of toluene and 5.0 g of ion exchange treated water were added thereto. Next, the admixture was neutralized by adding a 12% sodium hydroxide aqueous solution, after which this solution was cooled down for crystallization and filtered to obtain crude crystals The crude crystals were purified by recrystallization with a mixed solvent of water and methanol and then dried to obtain 7.7 g of the target product, 1,3,5-tris(4-hydroxyphenyl)adamantane, as white crystals (purity: 99.7%).

The yield against 1,3,5-adamantane-triol was 70.0% by mol.

Melting point: 217° C. (light transmittance method)

Molecular weight: 411.3 (M–H)$^-$ (mass spectrometry)

Proton nuclear magnetic resonance spectrum (solvent: DMSO, 400 MHz); formula 8:

Formula 8

| Assignment | δ | Signal | Number of protons |
|---|---|---|---|
| a | 9.1 | s | 3 |
| b | 6.7 | d | 6 |
| c | 7.2 | d | 6 |
| d | 2.3 | m | 1 |
| e, f, g, h, i, j | 1.8–2.0 | m | 12 |

EXAMPLE 9

1,3,5-Tris(3-cyclohexyl-4-hydroxyphenyl)adamantane

In a 200 ml four-necked flask equipped with a stirrer, a thermometer, and a reflux condenser were placed 7.5 g (0.04 mol) of 1,3,5-adamantane-triol and 70.4 g (0.4 mol) of 2-cyclohexylphenol, and the air in the reaction container was replaced with nitrogen, after which the temperature was raised to 90° C. Next, while maintaining the temperature, 3.8 g of p-toluenesulfonic acid monohydrate was added thereto and the reaction was carried out for 80 hours.

After the reaction, the temperature of the reaction mixture thus obtained was lowered to 80° C., and 75 g of toluene was added thereto. Next, 0.1 g of a 75% phosphoric acid aqueous solution and a 16% sodium hydroxide aqueous solution were added for neutralization. The water layer was separated from this mixture and the resulting oil layer was cooled down for crystallization, and filtered to obtain crude crystals containing the target product. The crude crystals were purified by recrystallization with a mixed solvent of isopropyl alcohol and water, and dried to obtain 4.9 g of the target product, 1,3,5-tris(3-cyclohexyl-4-hydroxy)adamantane, as white crystals (purity: 95.2%). The yield against 1,3,5-adamantane-triol was 19% by mol.

Melting point: 291° C. (differential thermal analysis)

Molecular weight: 657.8 (M–H)$^-$ (mass spectrometry)

Proton nuclear magnetic resonance spectrum (solvent: DMSO, 400 MHz); formula 9:

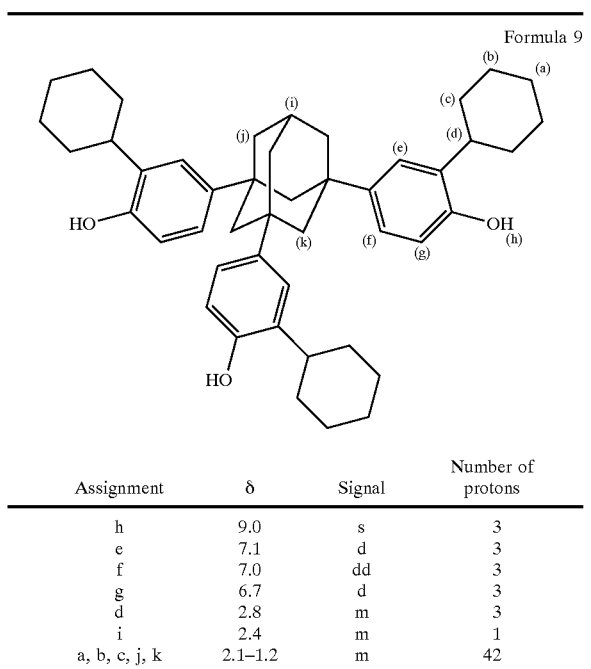

Formula 9

| Assignment | δ | Signal | Number of protons |
|---|---|---|---|
| h | 9.0 | s | 3 |
| e | 7.1 | d | 3 |
| f | 7.0 | dd | 3 |
| g | 6.7 | d | 3 |
| d | 2.8 | m | 3 |
| i | 2.4 | m | 1 |
| a, b, c, j, k | 2.1–1.2 | m | 42 |

Proton nuclear magnetic resonance spectrum (solvent: DMSO, 400 MHz); formula 10:

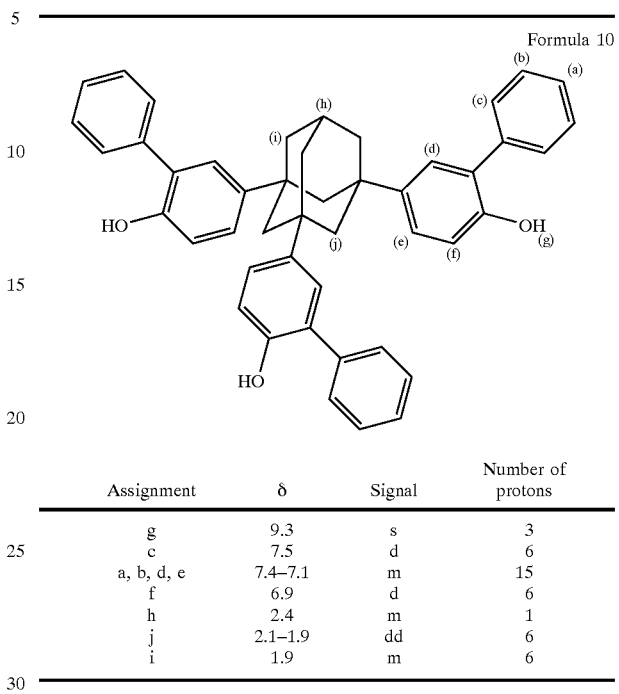

Formula 10

| Assignment | δ | Signal | Number of protons |
|---|---|---|---|
| g | 9.3 | s | 3 |
| c | 7.5 | d | 6 |
| a, b, d, e | 7.4–7.1 | m | 15 |
| f | 6.9 | d | 6 |
| h | 2.4 | m | 1 |
| j | 2.1–1.9 | dd | 6 |
| i | 1.9 | m | 6 |

EXAMPLE 10

1,3,5-Tris(3-phenyl-4-hydroxyphenyl)adamantane

In a 200 ml four-necked flask equipped with a stirrer, a thermometer, and a reflux condenser were placed 7.5 g (0.04 mol) of 1,3,5-adamantane-triol and 68.0 g (0.4 mol) of 2-hydroxy-1,1'-biphenyl, and the air in the reaction container was replaced with nitrogen, after which the temperature was raised to 90° C. Next, while maintaining the temperature, 3.8 g of p-toluenesulfonic acid monohydrate was added thereto and the reaction was carried out for 192 hours.

After the reaction, the temperature of the reaction mixture thus obtained was lowered to 80° C., and 68 g of toluene and 3.5 g of ion exchange treated water were added thereto. Next, 0.1 g of a 75% phosphoric acid aqueous solution and a 16% sodium hydroxide aqueous solution were added for neutralization. The water layer was separated from this mixture and the resulting oil layer was cooled down for crystallization, and filtered to obtain crude crystals containing the target product.

The crude crystals were purified by recrystallization with a mixed solvent of methylethyl ketone and toluene, and dried to obtain 10.9 g of the target product, 1,3,5-tris(3-phenyl-4-hydroxyphenyl)adamantane, as white crystals (purity: 92.8%).

The yield against 1,3,5-adamantane-triol was 43% by mol.

Melting point: 223° C. (differential thermal analysis)

Molecular weight: 639.5 (M–H)⁻ (mass spectrometry)

Novel hydroxyphenyl adamantanes of the present invention are bisphenols in which bulky hydroxyphenyl groups having substituent groups are bonded to an adamantane skeleton at positions 1 and 3 or trisphenols in which hydroxyphenyl groups optionally having substituent groups are bonded to an adamantane skeleton at positions 1, 3 and 5, and can be useful and excellent materials for improving heat resistance, mechanical strength characteristics, and the like when used as materials for epoxy resins, photosensitive resins, aromatic polycarbonate resins, and the like.

Further, these novel hydroxyphenyl adamantanes can be efficiently produced by reacting a 1,3-adamantane-diol or 1,3,5-adamantane-triol and phenols in the presence of an acid catalyst under reaction conditions that can be technically feasible without difficulty.

What is claimed is:

1. Hydroxyphenyl adamantanes represented by the general formula (1):

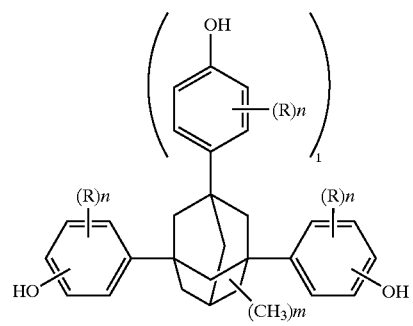

General formula (1)

wherein R is an alkyl group, cycloalkyl group or phenyl group; m is 0 or an integer 1 or 2; l is 0 or 1; when l is 1, hydroxy groups of substituted hydroxyphenyl groups at positions 1 and 3 are together in para-position; n is 0 or an integer 1, 2 or 3; and when l is 0, n is an integer 1, 2 or 3.

2. 1,3-Bis(hydroxyphenyl)adamantanes represented by the general formula (2):

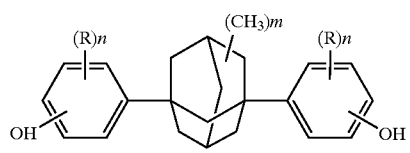

General formula (2)

wherein R is an alkyl group, cycloalkyl group or phenyl group, n is an integer 1, 2 or 3, and m is 0 or an integer 1 or 2.

3. 1,3,5-Tris(4-hydroxyphenyl)adamantanes represented by the general formula (3):

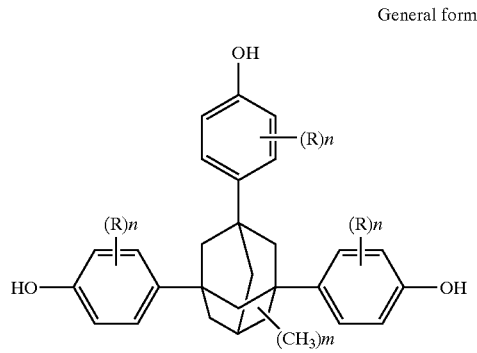

General formula (3)

wherein R is an alkyl group, cycloalkyl group or phenyl group, n is 0 or an integer 1, 2 or 3, and m is 0 or an integer 1 or 2.

4. A method of manufacturing 1,3-bis(hydroxyphenyl) adamantanes recited in claim 2, which comprises reacting 1,3-adamantane-diol represented by the general formula (4):

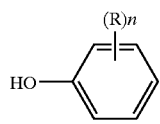

General formula (4)

wherein m is 0 or an integer 1 or 2, and substituted phenols represented by the general formula (5):

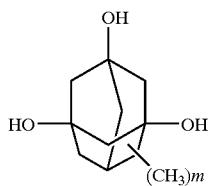

General formula (5)

wherein R and n are as defined in the general formula (2) above, in the presence of an acid catalyst.

5. A method of manufacturing 1,3,5-tris(4-hydroxyphenyl)adamantanes recited in claim 3, which comprises reacting 1,3,5-adamantane-triol represented by the general formula (6):

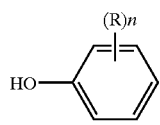

General formula (6)

wherein m is as defined in the general formula (3), and phenols represented by the general formula (7):

General formula (7)

wherein R and n are as defined in the general formula (3), in the presence of an acid catalyst.

* * * * *

UNITED STATES PATENT AND TRADEMARK OFFICE
CERTIFICATE OF CORRECTION

PATENT NO. : 6,720,460 B2
DATED : April 13, 2004
INVENTOR(S) : Akira Yoshikawa et al.

It is certified that error appears in the above-identified patent and that said Letters Patent is hereby corrected as shown below:

<u>Title page,</u>
Item [30], Foreign Application Priority Data, please change the priority number "2003-604245" to -- 2003-004245 --.

Signed and Sealed this

Sixth Day of July, 2004

JON W. DUDAS
*Acting Director of the United States Patent and Trademark Office*